(12) United States Patent
Liu et al.

(10) Patent No.: US 7,388,666 B2
(45) Date of Patent: Jun. 17, 2008

(54) PROBE ASSEMBLY WITH A LIGHT HOOD AND A DETECTING INSTRUMENT EQUIPPED WITH THE SAME

(75) Inventors: Encong Liu, Beijing (CN); Jinsheng Yu, Beijing (CN); Xiaolin Yang, Beijing (CN); Xiaodong Wu, Beijing (CN)

(73) Assignee: Beijing Yuande Bio-Medical Engineering Co., Ltd., Beijing (CN)

( * ) Notice: Subject to any disclaimer, the term of this patent is extended or adjusted under 35 U.S.C. 154(b) by 351 days.

(21) Appl. No.: 11/330,280

(22) Filed: Jan. 11, 2006

(65) Prior Publication Data

US 2006/0203249 A1 Sep. 14, 2006

(30) Foreign Application Priority Data

Mar. 8, 2005 (CN) .................... 2005 1 0054476

(51) Int. Cl.
*G03B 21/22* (2006.01)
*G01N 21/00* (2006.01)

(52) U.S. Cl. .................... 356/440; 353/75; 356/440

(58) Field of Classification Search ............ 353/74–78; 356/432–444
See application file for complete search history.

(56) References Cited

U.S. PATENT DOCUMENTS

| | | | | |
|---|---|---|---|---|
| 1,644,331 A | * | 10/1927 | Exton | .......................... 356/414 |
| 3,838,925 A | * | 10/1974 | Marks | .......................... 356/438 |
| 4,498,782 A | * | 2/1985 | Proctor et al. | .............. 356/436 |
| 5,305,081 A | * | 4/1994 | Gooch et al. | ................ 356/428 |
| 5,447,687 A | * | 9/1995 | Lewis et al. | .................. 422/52 |
| 6,052,184 A | * | 4/2000 | Reed | .......................... 356/338 |
| 6,123,903 A | | 9/2000 | Tajima | |
| 6,175,676 B1 | * | 1/2001 | Sharan | ....................... 385/100 |
| 2003/0143752 A1 | * | 7/2003 | Feldsine et al. | ............ 436/164 |

FOREIGN PATENT DOCUMENTS

| | | |
|---|---|---|
| CN | 2056758 U | 5/1990 |
| JP | 5-157699 | 2/1993 |

OTHER PUBLICATIONS

International Search Report dated Dec. 2005.

* cited by examiner

*Primary Examiner*—L. G. Lauchman
*Assistant Examiner*—Jarreas C Underwood
(74) *Attorney, Agent, or Firm*—Harness, Dickey & Pierce, P.L.C.

(57) ABSTRACT

A probe assembly used in testing instrument for determining optical signal within a test cell, comprising a top plate (5;205) with a through-hole (52;250) therein; a cylindrical light hood (2;202) having a central channel (21;221); the lower end of the optical pickup (1) is inserted into said channel (21;221) and surrounded by said light hood, and said light hood can slide down and up within a small distance isolating said one test cell of the sample being detected from its adjacent cells and surroundings when the lower end of said light hood is in said protruding position, so that the light interference from the adjacent test cells and surroundings with (to) the determination of the sampling being detected can be avoided. Also, the present invention further relates to the light hood included in the probe assembly and the instruments including the probe assembly.

13 Claims, 10 Drawing Sheets

US 7,388,666 B2

PROBE ASSEMBLY WITH A LIGHT HOOD AND A DETECTING INSTRUMENT EQUIPPED WITH THE SAME

TECHNICAL FIELD

The present invention relates to a testing device, more particularly, to a probe assembly used in medical testing devices for determining optical signal in a test cell, a medical testing device and a micro-cellular-plate single photon counting device for determining optical signal in a test cell.

BACKGROUND ART

Recently, there are various kinds of known testing instruments for determining optical signal. Its principle is that the optical signal picked up or determined by a photo electric converter (transducer) is converted into voltage or current signal and then these voltage and current signal is amplified. With the quantum physics developing, a novel high-sensitivity photoelectric testing device so called a single-photon counting device has been manufactured and widely used in aviation, space-flight, military affairs, medical treatment, security, scientific research, environmental protection, agriculture, and industry etc. An example of applying a single photon counter in medical field is a micro-cellular-plate-single-photon counting device with it, widely applied in various aspects of the clinic diagnosis, such as gene analysis, determinations of hormones, medicines, vitamin, and materials related to cancers and infections. Generally, the micro-cellular-plate-singe-photon counting device is consisted of a probe; more than one test cell; a transporter mechanism carrying the test cells; a housing; a controller; a central computer. The sequential steps of the determination process of the micro-cellular-plate-single-photon counting device are below: putting the prepared sample into a test cell and then placing the test cells into sample container (namely, micro-cellular-plate, e.g., a micro-cellular-plate with an array of 12 rows by 8 columns of test cells, i.e. 96 test cells); putting the sample container, i.e. the micro-cellular plate, onto a bracket; covering the housing; delivering the bracket with the micro-cellular plate on it into the housing in a light-sealing state by the transporter mechanism when the device switch is turned on; and determining the samples in the test cells one by one by movement of the optical pickup of the counting device in relation to the sample container.

Since the micro-cellular plate single photon counting device is an instrument which determines the number of photons within the test cell, the light-sealing of the device must conform to a severe requirement.

The probe used in the prior art is shown in FIG. 17. FIG. 17 shows the relationship of the optical pickup 1 and a plurality (e.g. 96) of the test cells 6 arranged one by one integrally or put into a contiguous relation on the 96-site micro cellular plate during one of the sample being determined. The test cells are disposable plastic products. The flush of their mouths is poor and also fluctuations of the height exist among plurality of the test cells, which can cause a light cross interference between the determined samples(namely, a secondary light seal defect). Said light cross interference refers to that the optical pickup is influenced by the light from the adjacent test cells, leading to an error in the determination of the sample being detected since the top of the test cell being detected or the top of its adjacent test cells can't closely abut against the top plate 102 of the housing due to the poor flush and the fluctuations of the heights of test cells. The determining results can be substantially influenced especially when the strength of light from the samples of the adjacent test cells is relatively high while that of the sample being detected is relatively low.

SUMMARY OF THE INVENTION

An object of the present invention is to provide a novel probe assembly which can be used in a device such as a medical testing instrument for determining the optical signal of sample within a test cell, like a single photon counting device in order to overcome the light-seal defect of the prior art.

An other object of the present invention is to provide a novel testing instrument for determining optical signal of sample within a test cell including said probe assembly of the present invention.

A further other object of the present invention is to provide a novel micro-cellular plate single photon counting device including said probe assembly of the present invention.

According to a first aspect of the present invention, there is provided a probe assembly used in testing instrument for determining optical signal within a test cell, comprising:

a top plate with a through-hole therein;

an optical pickup connecting with a photoelectrical converter for picking up optical signal within a test cell and sending said optical signal to said photoelectric converter converting said optical signal to electric signal, wherein the position of said optical pickup in relation to said top plate is fixed, the lower end of said optical pickup is inserted into said through-hole of said top plate and said optical pickup determines the sample in one of the test cells adjacently arranged or integrally connected, when said one of the test cells is delivered by a transporter mechanism to the position where it is exactly under said through-hole of said top plate with the top mouth of said one of the test cells being exactly aligned with the lower end of said optical pickup, to obtain optical signal;

a cylindrical light hood having a central channel, partially inserting into said through-hole of said top plate, and constructed in such a manner that the lower end of said optical pickup is inserted into said channel and surrounded by said light hood and said light hood can slide down and up along the longitudinal direction of said optical pickup and said through-hole within a small distance between a protruding position and a retracting position, wherein said light hood lies in said retracting position through sliding up, while said light hood lies in said protruding position through sliding downward in the case the one test cell of the sample to be determined is delivered by said transporter mechanism to the place where it is exactly under said through-hole and aligned with the lower end of said optical pickup, so that the light interference from the adjacent test cells and surroundings with (to) the determination of the sample being detected can be avoided by isolating said one test cell from its adjacent cells and surroundings by said light hood when the lower end of said light hood is in said protruding position with the size of the lower end of said light hood tightly matching the size of the top mouth of said test cell.

The advantage of the first aspect of the present invention is that because said optical pickup is provided with said light hood surrounding it, the lower end of said light hood can contact with the top or the outside of the top of the test cell being determined, or somewhat insert into the joint between the test cell being detected and its adjacent test cells through sliding down during determining one sample, thereby the light from the, outside of the sample being detected is blocked, namely the optical pickup is prevented from being influenced by the outside light. Also, the light hood has an other function to block the light leaked through said housing.

According to a preferable embodiment, there is a clearance between said light hood and said optical pickup to prevent said optical pickup from being disturbed by the vibration generated during said light hood sliding.

Preferably, said probe assembly according to present invention may comprise a guide bushing having a central sliding passage for said light hood sliding therein and an internal size and contour fitted with the external size and contour f said light hood, inserted into said through-hole of said top plate in a light seal manner and fixed on said housing with said light hood interposed between the outer wall of said optical pickup and the inner wall of said guide bushing to guide said light hood to slide up and down therein.

Said guide bushing allows said light hood to slide up and down smoothly.

Preferably, said guide bushing is formed with a stop portion and said light hood is formed with a support portion abutting against said stop portion when said light hood lies in said protruding position through sliding downward, so that a further sliding downward of said light hood is stopped.

Preferably, said stop portion may be formed at the upper end of said guide bushing and said support portion may be formed by a flange at the upper end of said light hood. However, it can be understood for the skilled in the art upon reading this disclosure that said support portion can be formed at other portions of said light hood, e.g. at the outside of the middle of said light hood. Also, said stop portion may be formed at the other portions of said guide bushing. For example, a sliding chute extending up from the middle of said guide bushing may be formed for said support portion of said light hood to slide on it. In this case, said chute and said support portion function as a guide while the bottom of said chute and said support portion function as a stopper.

The present invention may further comprise a force-applying mechanism for allowing said light hood to slide to said protruding position, or for allowing said light hood to slide to said protruding position and back to said retracting position. The action of said force-applying mechanism is to ensure said light hood to reliably slide up or down as necessary.

Preferably, an inner circumferential chamfer and an outer circumferential chamfer merging with the inner chamfer to form a circumferential tip may be formed at the lower end of said light hood. Preferably, said force-applying mechanism may comprise at least one spring each in C shape with its lower end fixed to the housing and its upper end in contact with said light hood in order to apply a predetermined downward pressure to said light hood, so that said light hood normally lies in said protruding position due to the action of the downward pressure, but said light hood can be slidden down or up by the downward pressure of said spring or a up pushing force generated when the top of one of the plurality of the test cells contact with said chamfers of said light hood, during the movement of the micro-cellular plate carrying said a plurality of the test cells, wherein said circumferential tip formed by the chamfers at the lower end of said light hood is inserted into the joint between the test cell being detected and its adjacent cells, when said light hood lies in said protruding position and also said circumferential tip is aligned with said joint close, therefore the interference with the determination of the sample being detected by its adjacent test cell and surroundings can be prevented. Said light hood can freely and smoothly slide up by the up pushing force generated during the outer circumferential chamfer contacting (interacting) with the mouth of the test cell.

Alternatively, said force-applying mechanism may be a electric motor which is fixed to said housing and drive said light hood to slide up and down through a transmitting mechanism under controlling of a control circuit as necessary. The skilled in the art can appreciate the concrete embodiment about the above motor, though there is no further description herein, Preferably, an outer circumferential chamfer with a arc cross-section fitted with the circumferential chamfer of the lower end of said light hood may be formed at the outer circumference of the mouth of the test cell, so as to make the sliding of said light hood smoother. The inner circumferential chamfer of the lower end of said light hood exactly abuts on said circumferential chamfer when said light hood lies in its protruding position to further enhance the light seal effect.

Preferably, said optical pickup is optic tube and said photoelectric converter is a photomultiplier assembly.

According to an other preferable embodiment, said spring is made of a stainless steel wire, and the predetermined pressure exerted on the said light hood by said spring is about 0.05 N, which can ensure said light hood to slide downward to effect a good light seal.

According to an other preferable embodiment, said force-applying springs comprise 4 springs arranged circumferentially at a regular interval around said light hood and fixed to said top plate, thereby to make the force exerted on said light hood circumferentially distribute in a uniform manner, so as to ensure no tilting during the sliding of said light hood.

According to a preferable embodiment, a simple structure which may be employed to fix said guide bushing and the force-applying spring to said top plate is as follows: a fixing flange with fixing through-holes is formed at the outer circumference of the lower portion of said guide bushing and a fixing ring is formed at each lower end of said force-applying springs, threaded holes are formed at said top plate, so both said guide bushing and said force-applying mechanism are fixed to said top plate by fastening screws passing through said fixing rings and said fixing though-holes into said threaded holes.

Since said circumferential chamfers at the lower end of said light hood constitute the circumferential tip, the lower end of said light hood is inserted into the joint between the test cell being detected and the its adjacent test cells and contacts with the top of the former when the light hood lies in said protruding position, thereby a light seal is formed. The inner circumferential chamfer of the lower end of said light hood forms an opening in a truncated cone shape which can engage with the top mouth of the test cell or the outer circumferential chamfer of its top to ensure a good light seal due to the lower end reliably contacting with the top of the test cell.

Preferably, said light hood is made of an abrasion-resistant material of low friction coefficient.

Preferably, said light hood is made of polytetrafluoroethylense or bronze and said guide bushing is made of bronze.

Preferably, all said light hood, said guide bushing and said optical pickup are cylindrical, the radial clearance between the inner wall of said light hood and the outer wall of said optical pickup is 0.3-0.4 mm.

While the sliding of said light hood is effected by said force-applying springs or electric motor, as mentioned above, this slide also can be driven by the gravity of itself. According to a preferable embodiment corresponding to this principle, said light hood is formed with a upper flange at its upper portion having such a great diameter that said flange radially extends beyond the inner surface of the through-hole of said top plate and said light hood has such a great weight that in a normal condition, said upper flange abuts on the peripheral edge of said through-hole, causing said light hood to lie in said protruding position due to the action of its gravity, while said light hood can be slid up by the up pushing force exerted by the mouth of the test cell to its lower end. Besides, this embodiment can be improved as below:

Preferably, said light hood may have: a middle portion with a reduced diameter forming a annular groove around it, with a clearance between its outer wall and the inner wall of the through-hole of said top plate to form a loose fit between said light hood and said through-hole; a lower outer flange, formed at the lower portion of said light hood, and having its outer contour and size fitting with the inner contour and size of said through-hole of said top plate, and being guided by said through-hole. Since there is a loose fit between said light hood and said through-hole and the length of the lower outer flange used in the guiding is relatively small, the sticking of said light hood during sliding up or down can be avoided.

Preferably, said light hood may have a lower inner flange opposite to said lower outer flange, both a lower inner circumferential chamfer and a lower outer circumferential chamfer merging with said lower inner circumferential chamfer to form a circumferential tip are formed at the radial outside of the peripheral edge off the lower inner flange bottom surface (a circumferential downward projection with a circumferential tip is formed at the radial outside of the peripheral edge of the lower inner flange bottom surface by a lower inner circumferential chamfer and a lower outer circumferential chamfer), with the area in the radial inside of the bottom surface of said lower inner flange being flat. Such structure facilitates the smooth motion of the test cells in relation to the light hood. With a plurality of test cells placed on the micro-cellular plate, said light hood slides down and up respectively by its gravity and a up pushing force generated when the top of the test cell comes in contact with the chamfers of the lower inner flange of said light hood during the moving the micro-cellular plate with the test cells, and finally the circumferential tip formed by both the chamfers inserts into the joint between the test cell being detected and its adjacent cells, as the tip is aligned with the joint close.

Preferably, said light hood is made of bronze.

According to a second aspect, there is provided a testing instrument for determining optical signal within a test cell, comprising: the probe assembly as said in the first aspect of the present invention and further comprising:

a housing for isolating said test cells in said housing from the outside surroundings in a light seal manner when at least one said test cell is delivered into said housing;

wherein said optical pickup is fixedly connected to the end of said photoelectric converter relatively fixed to the housing;

said transporter mechanism is relatively fixed to said housing;

in operation, more than one test cell integrally connected or adjacently arranged on a micro cellular plate is carried by said transporter mechanism;

said transporter mechanism can carry and deliver said micro-cellular plate with the test cells on it so as to move said test cells in a condition that their tops abut against or leave a certain clearance below the lower surface of said top plate, and sequentially to make the top mouth of each the test cells reach the position below the through-hole and align with the optical pickup to allow said optical pickup to pick up a signal from the test cells one by one.

According to a third aspect, there is provided a micro-cellular plate single photon counting device, comprising: the probe assembly as said in the first aspect or its preferable embodiments and further comprising:

a housing for isolating said test cells from the outside surroundings in light seal manner when at least one said test cell is delivered into said housing;

a single photon counter, fixed to said housing and includes said photoelectric converter fixedly connecting said optical pickup at its end;

wherein said transporter mechanism is fixed to said housing;

in operation, more than one test cell integrally connected or adjacently arranged on a micro cellular plate is carried by said transporter mechanism;

said transporter mechanism can carry and deliver said micro-cellular plate with the test cells on it so as to move said test cells in a condition that their tops abut against or leave a certain clearance below the lower surface of said top plate, and sequentially to make the top mouth of each the test cells reach the position below the through-hole and align with the optical pickup to allow said optical pickup to pick up a signal from the test cells one by one.

According to a fourth aspect, there is provided a cylindrical light hood used in a testing instrument for determining optical signal in a test cell, said light hood having: a central channel; a portion inserted into a through-hole of the top plate of said testing instrument; and a size and a contour constructed to allow the lower end of the optical pickup of said testing instrument to insert into said channel and to be surrounded by said light hood, and also the size of the lower end of said light hood being fitting with the size of the top mouth of said test cell, so said light hood can isolate the top mouth of the test cell of the sample being detected from the surroundings in light seal manner when the lower end of said light hood is aligned with the top of the test cell.

Preferably, an inner and an outer circumferential chamfers merging a circumferential tip are formed at the opening of the channel and the outer side of the lower end of said light hood, respectively;

an upper outer flange is formed at the upper end of said light hood.

Preferably, said light hood is made of a material with a low friction coefficient.

Preferably, said light hood is made of polytetrafloroethylene or bronze.

Preferably, both said light hood and said optical pickup are cylindrical and the clearance between said light hood and said optical pickup is 0.3-0.4 mm.

Said upper outer flange at the upper end of said light hood has such a great diameter that said flange radially extends beyond the inner wall of the through-hole of said top plate and said light hood has such an adequate weight that in a normal condition, said upper outer flange abuts on the peripheral edge of said through-hole, causing said light hood to lie in said protruding position due to the action of its gravity, while said light hood can be slid up by the up pushing force exerted by the mouth of the test cell to its lower end.

Said light hood further have: a middle portion with a reduced diameter forming a annular groove around it, with a clearance between its outer wall and the inner wall of the through-hole of said top plate to form a loose fit between said light hood and said through-hole; a lower outer flange with its outer contour and size fitting with the inner contour and size of said through-hole of said top plate, formed at the lower portion of said light hood, and having an outer chamfer formed at its bottom, thus lying in being guided by said through-hole.

Preferably, said light hood may further have a lower inner flange opposite to said lower outer flange, wherein both a lower inner circumferential chamfer and a lower outer circumferential chamfer merging with said lower inner circumferential chamfer to form a tip are formed at the radial outside of the peripheral edge of the lower inner flange bottom surface(a circumferential downward projection with a circumferential tip is formed at the radial outside of the peripheral edge of the lower inner flange bottom surface by a lower inner circumferential chamfer and a lower outer circumferential chamfer), with the area in the radial inside of said lower inner flange bottom surface being flat.

The effects and advantages of the second, third and fourth aspects of the present invention is the same that mentioned with respect to the first aspect.

PREFERABLE EMBODIMENTS

Figure 1:
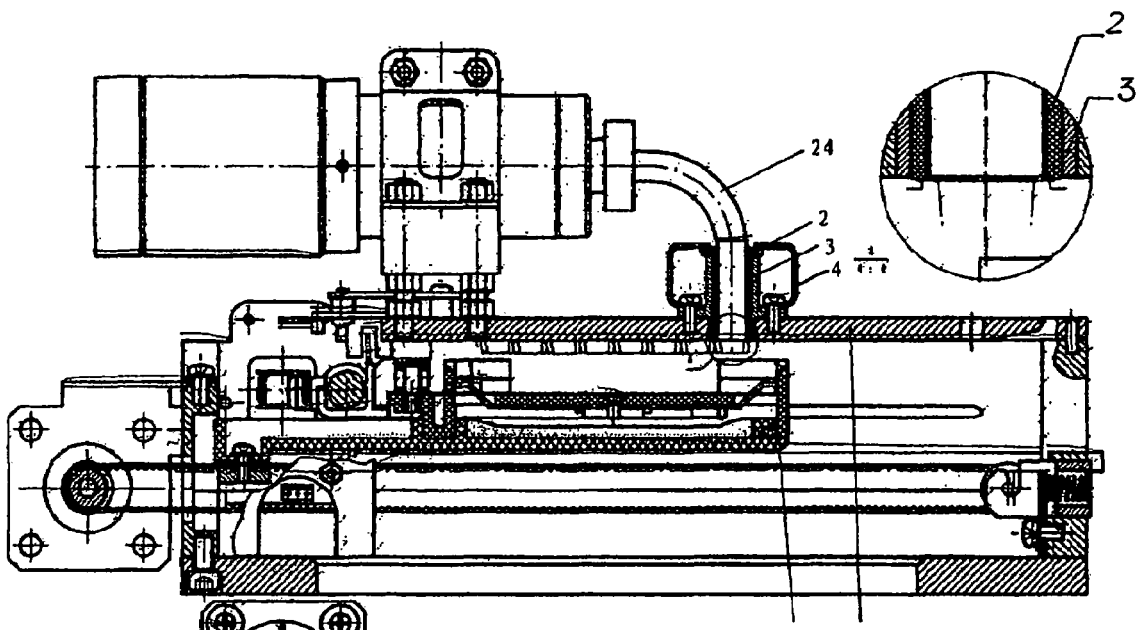
FIG. 1 is a vertical sectional view of a single photon counting device according to a preferable embodiment of the present invention.
Figure 2:
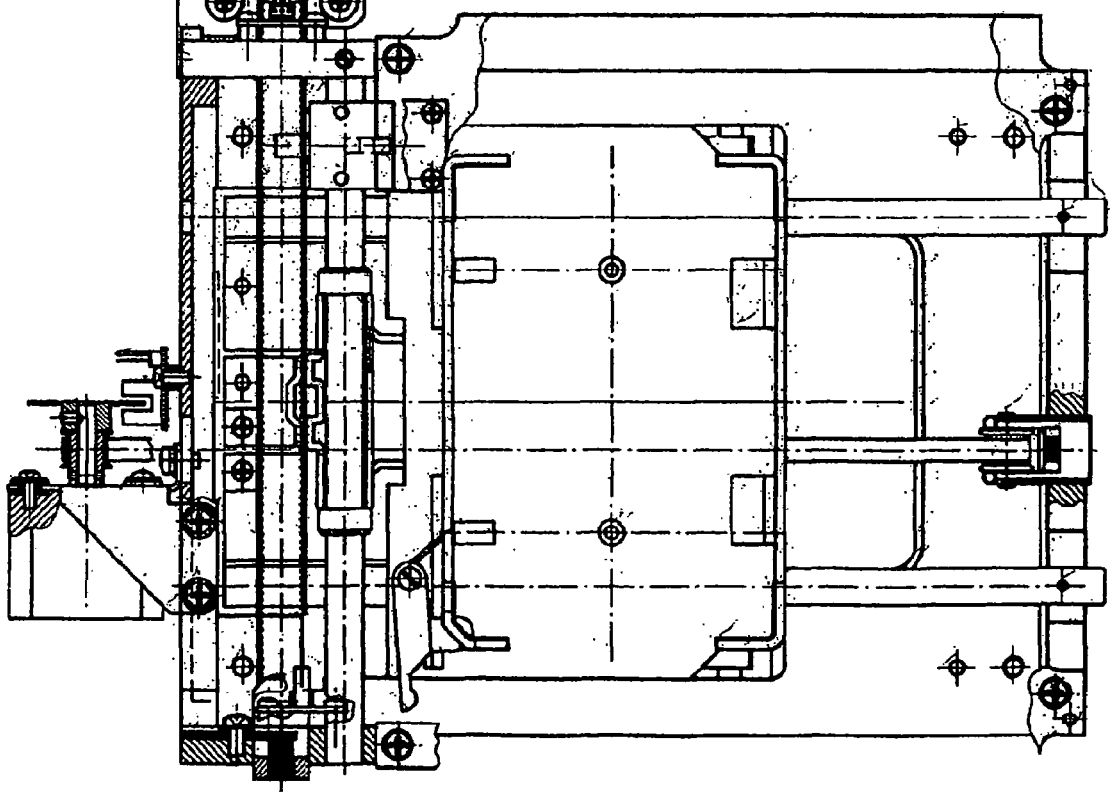
FIG. 2 is a horizontal sectional schematic view of a single photon counting device according to a preferable embodiment of the present invention.

FIG. 1 and 2 show the micro-single photon counting device according to the preferable embodiment of the present invention, which comprises the probe assembly according to the preferable embodiment of the present invention, as its part. At first, said probe assembly will be described in detail in conjunction with FIG. 3-14.

Figure 3:
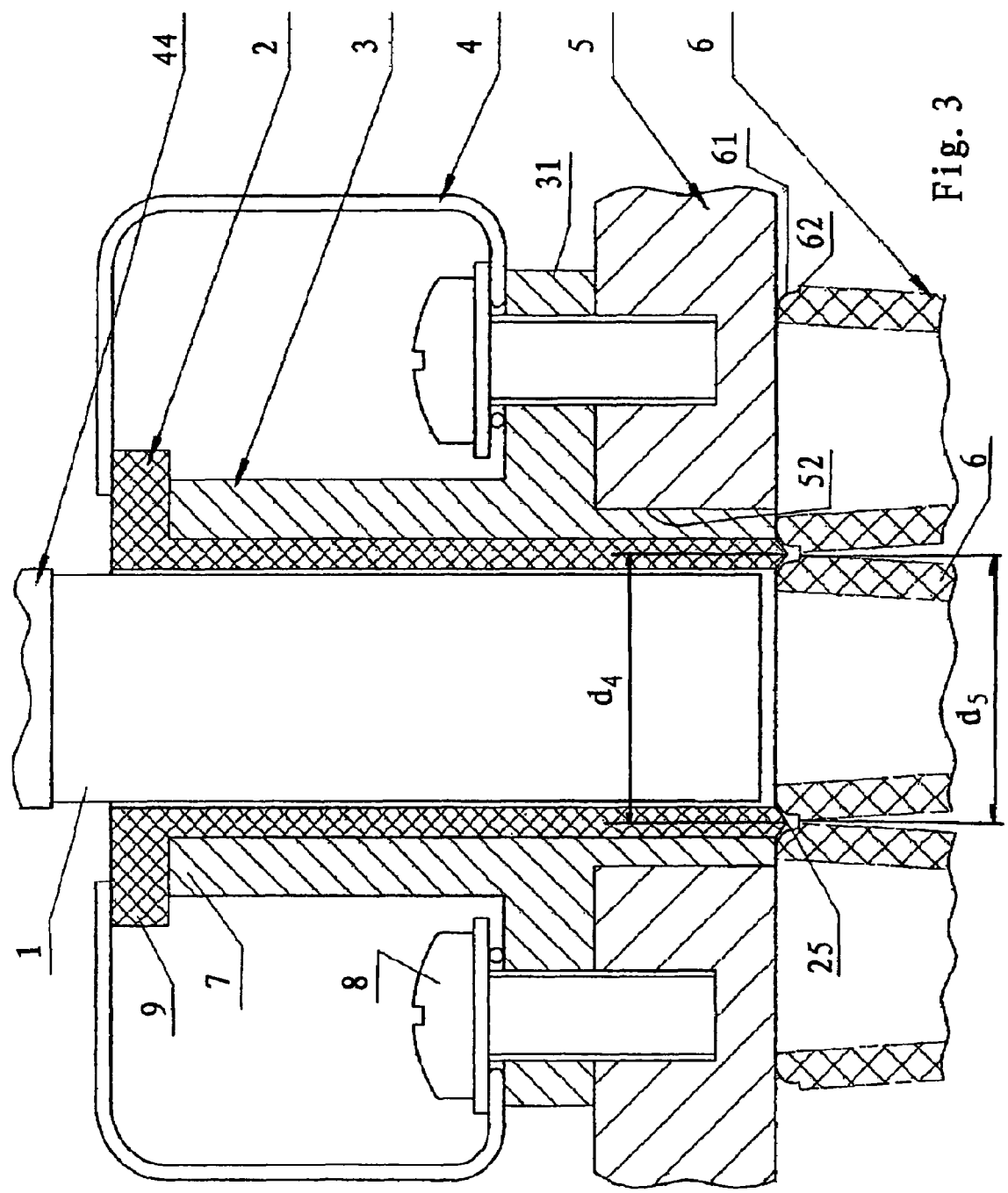
FIG. 3 is a sectional schematic view of a probe assembly according to a preferable embodiment of the present invention.
Figure 4:
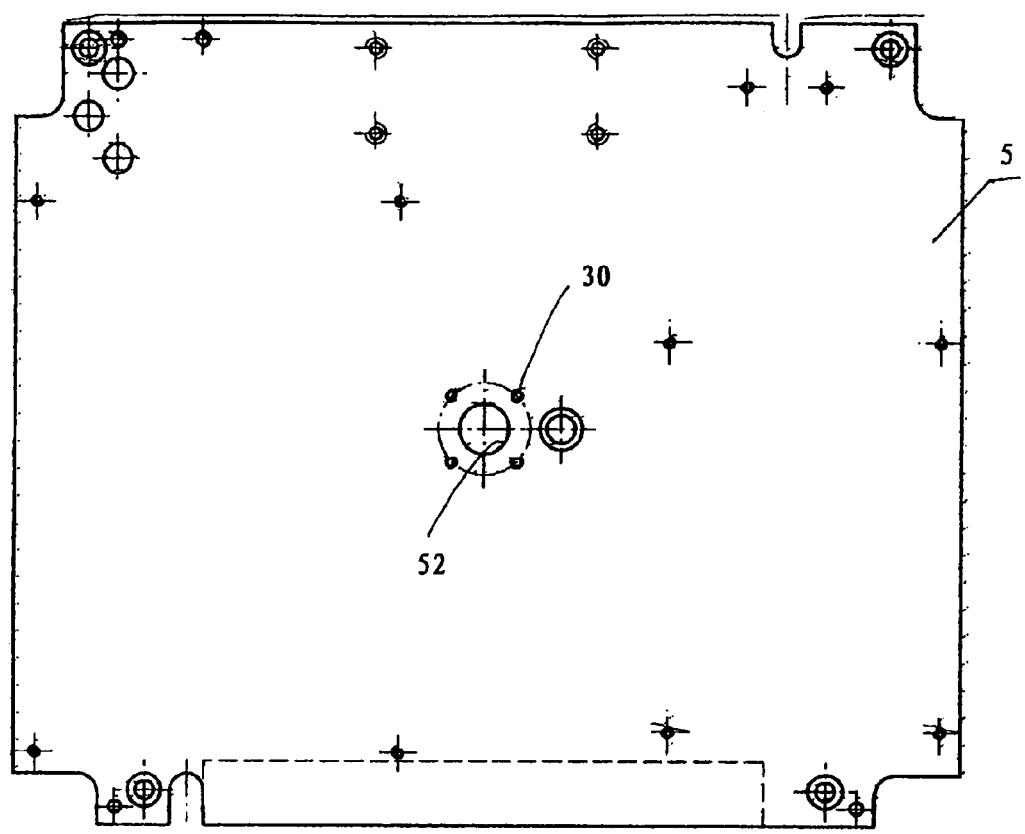
FIG. 4 is a plan schematic view of the top plate used in a probe assembly or a single photon counting device according to a preferable embodiment of the present invention.
Figure 5:
FIG. 5 is a vertical sectional schematic view of a top plate used in a probe assembly or a single photon counting device according to a preferable embodiment of the present invention.
Figure 6:
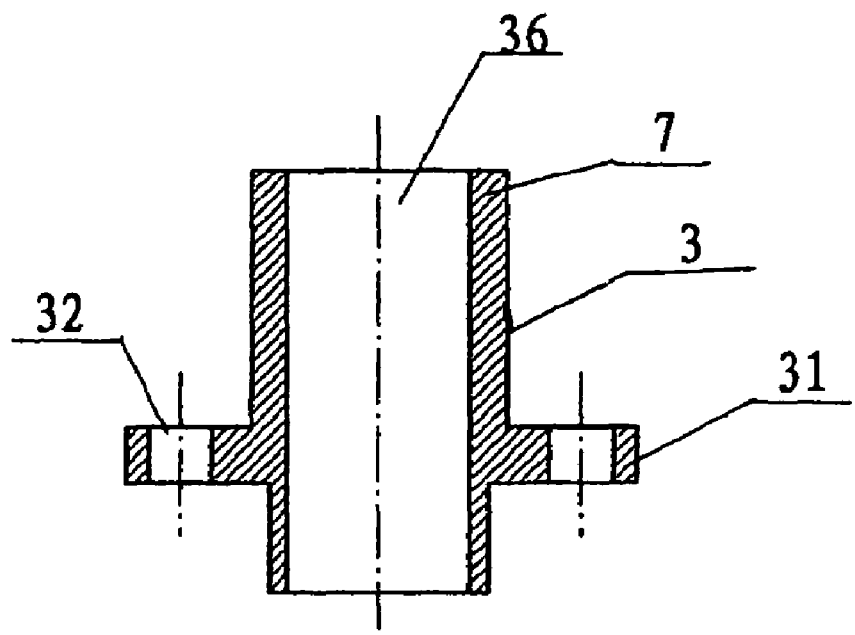
FIG. 6 is a vertical sectional schematic view of a guide bushing of a probe assembly according to a preferable embodiment of the present invention.
Figure 7:
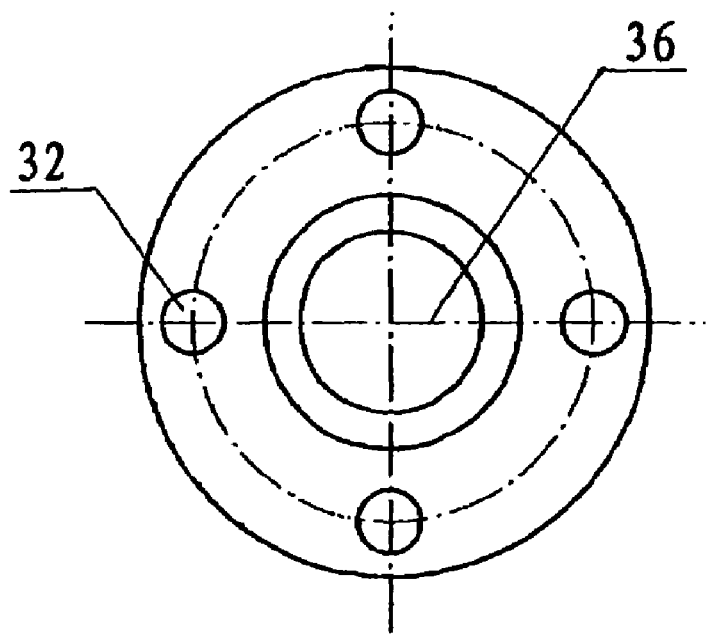
FIG. 7 is a plan schematic view of a guide bushing of a probe assembly according to a preferable embodiment of the present invention.
Figure 8:
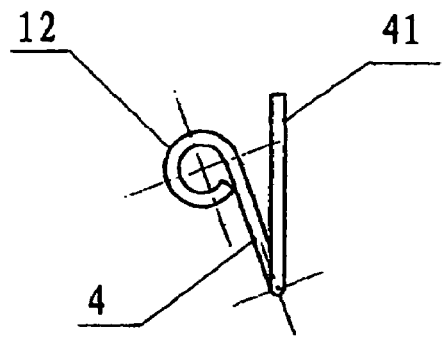
FIG. 8 is a plan schematic view of a force-applying spring of a probe assembly according to a preferable embodiment of the present invention.
Figure 9:
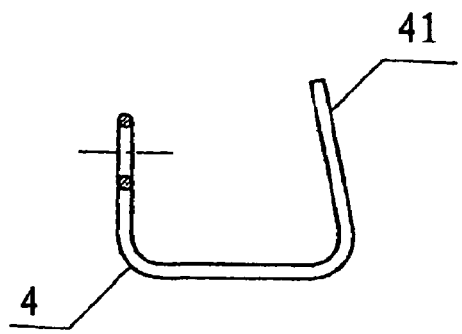
FIG. 9 is a partially sectional schematic view of a force-applying spring of a probe assembly according to a preferable embodiment of the present invention, viewed from left side of FIG. 8.
Figure 10:
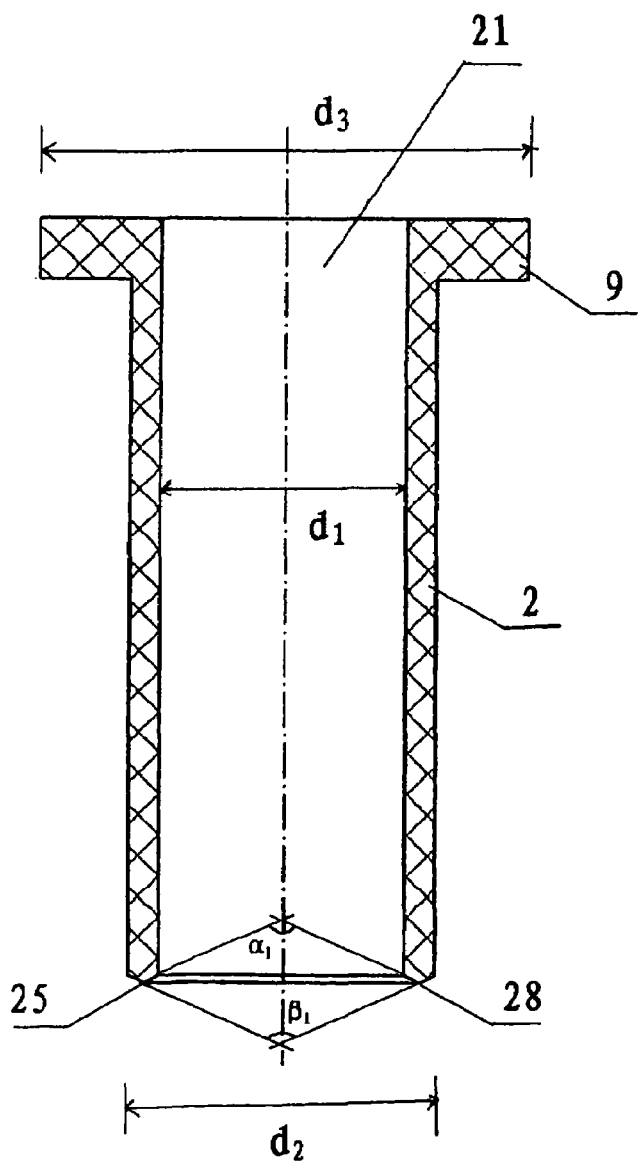
FIG. 10 is a sectional schematic view of a light hood of a probe assembly according to a preferable embodiment of the present invention.
Figure 11:
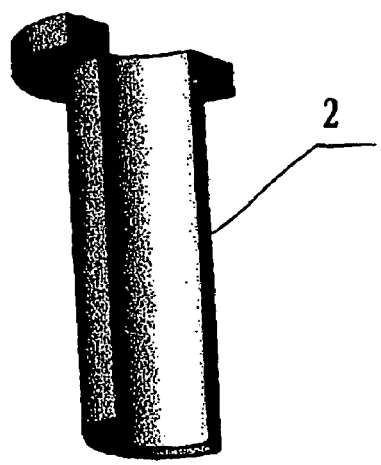
FIG. 11 is a sectional perspective view of a light hood of a probe assembly according to a preferable embodiment of the present invention.

As shown in FIG. 3, a probe assembly used for a testing instrument determining optical signal in a test cell comprises: a top plate 5, constituting a part of the single photon counting device and the cover plate of it, formed with a through-hole 52; a cylindrical optical pickup 1, connecting with a photoelectric (photovoltaic) converter for picking up the optical signal of the sample in the test cell 5 and sending the picked signal to the photoelectric converter converting the picked optical signal to a electrical signal. In this embodiment, said optical pickup is a fiber optical tube, and said photoelectric converter is a photomultiplier assembly 24. The position of said optical pickup in relation to said top plate 5 is fixed, namely the optical pickup is fixedly connected to the photomultiplier assembly 24 and in turn photomultiplier assembly 24 is fixed to the top plate.

The probe assembly of the invention further comprises a cylindrical light hood 2 and a cylindrical guide bushing 3, but the guide bushing is not necessary. In the second embodiment of the invention shown in FIG. 12, the probe assembly is not provided with a guide bushing. The light hood 2 and the bushing 3 may be made of a material having a small friction coefficient in order to ensure their abrasion resistance and the smooth sliding in relation to each other. In this embodiment, the light hood 2 is formed of polytetrafluoroethylene and the bushing is formed of bronze. However, the present invention is not limited therein. In the embodiment shown in FIG. 12-14, the light hood is formed of bronze.

The light hood 2 has a central channel 21 passing through it and he guide bushing 3 has a central sliding passage passing through it for the light hood to slide in it. The internal contour and size of the guide bushing 3 are fitted to the external contour and size of the light hood 2.

A fixing flange 31 with a plurality of through-holes serving as fixing is formed at the lower portion of the guide bushing 3. The lower portion of the guide bushing 3 is inserted into the through-hole of the top plate 5 to make the flange 31 abut against the top plate 5.

In this embodiment, the probe assembly further comprises 4 force-applying springs 4. However, the springs is not necessary and instead its function can be accomplished by a motor or by means of the gravity of the light hood. Also, the number of the springs can be changed, for example, only one spring can be used.

In this embodiment, the force-applying springs are in the form of "C". A ring 12 for fixing is formed at the lower end of each spring 4. 4 threaded holes are formed on the top plate 5. The guide bushing 3 and the spring 4 are together fixed on the top plate 5 by fastening screws 8 passing through a washer, the ring 12 and the through-holes 32 into the threaded holes. Alternatively, other methods for fixing the guide bushing and springs to housing may be adopted. The 4 threaded holes are circiumferentially arranged at a regular interval around the light hood so that the fixed 4 springs are circumferentially positioned in equal interval between the adjacent two around the light hood 2.

The light hood 2 is inserted into the sliding passage 36 of the guide bushing 3 and is placed between the external wall of the optical pickup 1 and the internal wall of the guide bushing 3. The lower end of the optical pickup 1 is inserted into the channel 21 of the light hood 2 and is surrounded by the light hood 2. The light hood can slide up and down along the longitudinal direction of the optical pickup 1 and the through-hole 52 of the top plate 5 by a small distance under the guiding of the guide bushing 3.

A stop is formed at the upper end 7 of the guide bushing 3. A flange 9 is formed at the upper end of the light hood 2, which serves as support portion abutting against the stop to make the light hood stop at a position where its lower end lies in a protruding position and impossible to further slide downward during the course of the light hood 2 sliding downward.

The upper end of the springs 4 is placed on flange 9 of the light hood 2, to apply a predetermined force to the light hood 2, so that the lower end of the light hood 2 lies in said protruding position. In this embodiment, the springs 4 is made of stainless steel wire and the predetermined force applied by the springs to the light hood is 0.05N.

Although the light hood 2, the guide bushing 3 and the optical pickup of this embodiment are all cylindrical, the present invention is not limited therein. The inner diameter of the light hood is larger than the outer diameter of the optical pickup with 0.3-0.4 clearance therebewteen, to prevent the vibration caused by the up and down sliding of the light hood from disturbing the optical pickup.

The circumferential chamfers are formed on the inner and outer circumferences of the lower end of the light hood 2, making a circumferential tip 25 at the place where the chamfers merge.

In the operation of determination, one 6 of the samples cells arranged side by side and delivered by the transporter mechanism is moved to below the through-hole 52 of the top plate with the top mouth of said one test cell 6 being aligned with the lower end of the optical pickup 1 to allow the optical pickup to pick up a signal of the sample.

The light hood 2 is slid down or up by the downward pressure applied by the springs 4 and the up pushing force generated when the chambers come in contact with the top of the test cell, while the micro-cellular plate carrying at least one of the test cell is moved, and consequently the circumferential tip at the chamfered lower end of the light hood is inserted into the joint between the adjacent test cells when the circumferential tip 25 is aligned with the joint close.

The lower end of the light hood 2 can lie in a protruding position when it is sliding downward, and its lower end can lie in a retracked position when it is going up. Upon the sample being determining, the lower end of the light hood 2 is in said protruding position through sliding downward when the test cell 1 of the sample being detected reaches the position exactly under the through-hole of the top plate and is aligned with the lower end of the optical pickup by delivering by the transporter mechanism. As the lower end size of the light hood is matched with the top mouth size of the test cell, the light hood can isolate the top opening from its light surroundings in order to prevent the cross interference of the light from its surroundings and the adjacent test cells when the lower end of the light hood is in said protruding position.

As a applying-force mechanism, the springs 4 act a downward force upon the light hood to cause the lower end of the light hood to slide into the protruding position. Alternatively, as the applying force mechanism the present invention may use a motor. The motor is used to move the light hood downward into the protruding position and back into the retracting position. The motor may be mounted to the housing. The motor is connected with the drive means of the light hood 2 through a transmitting member and controlled by a controlling circuit to drive the light hood to slide up or down as necessary.

Figure 12:
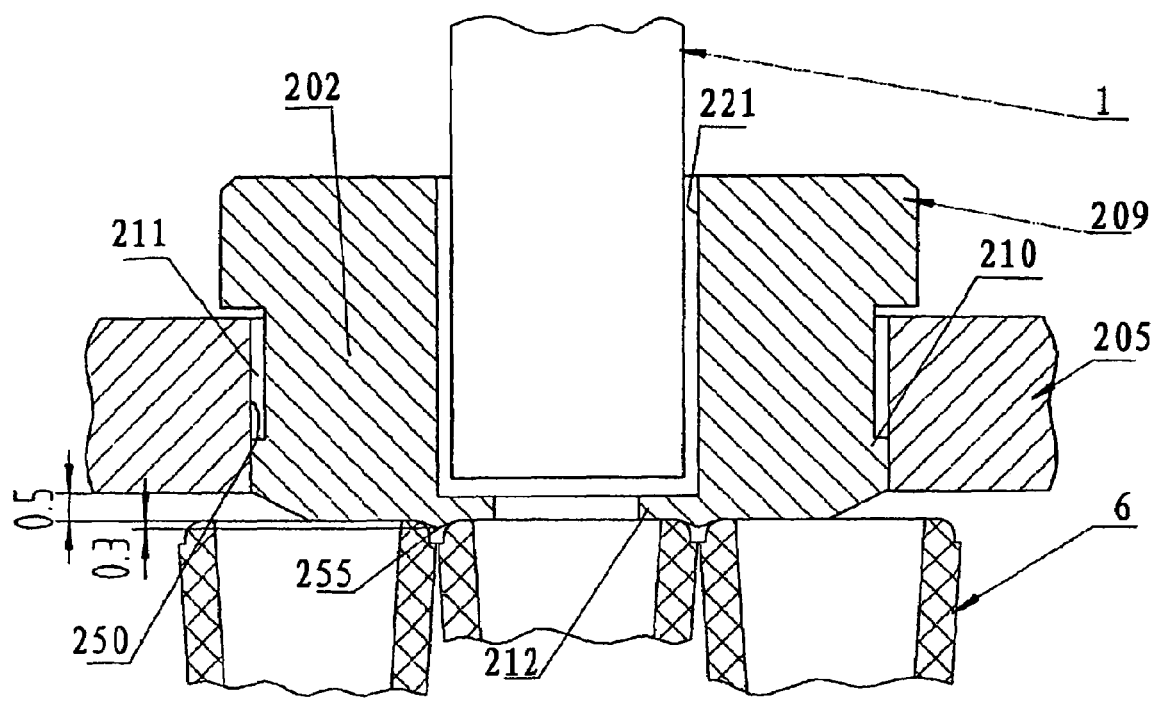
FIG. 12 is a sectional schematic view of a probe assembly used in a single photon counting device according to a second preferable embodiment of the present invention.
Figure 13:
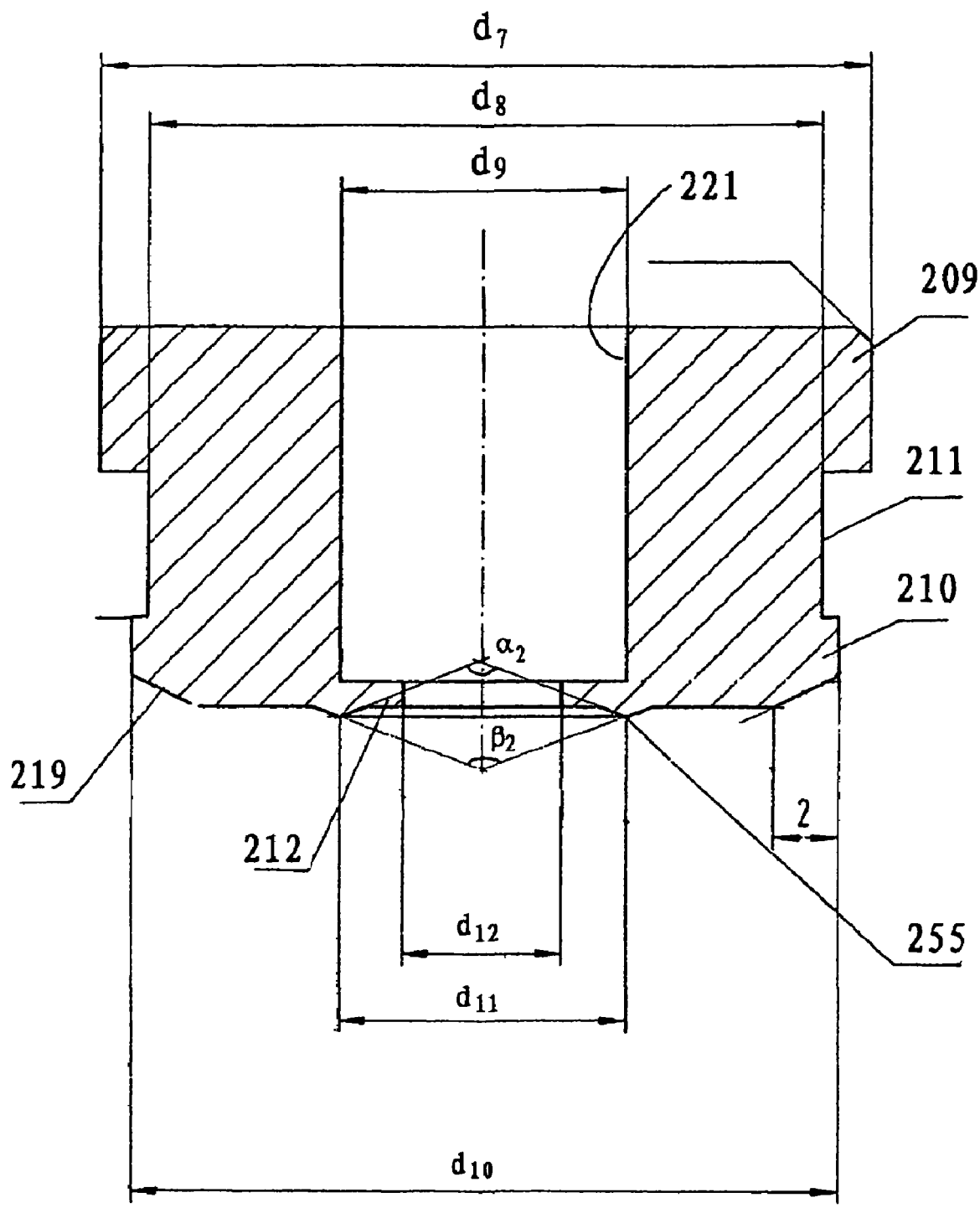
FIG. 13 is a sectional schematic view of a light hood of a probe assembly according to a second preferable embodiment of the present invention.
Figure 14:
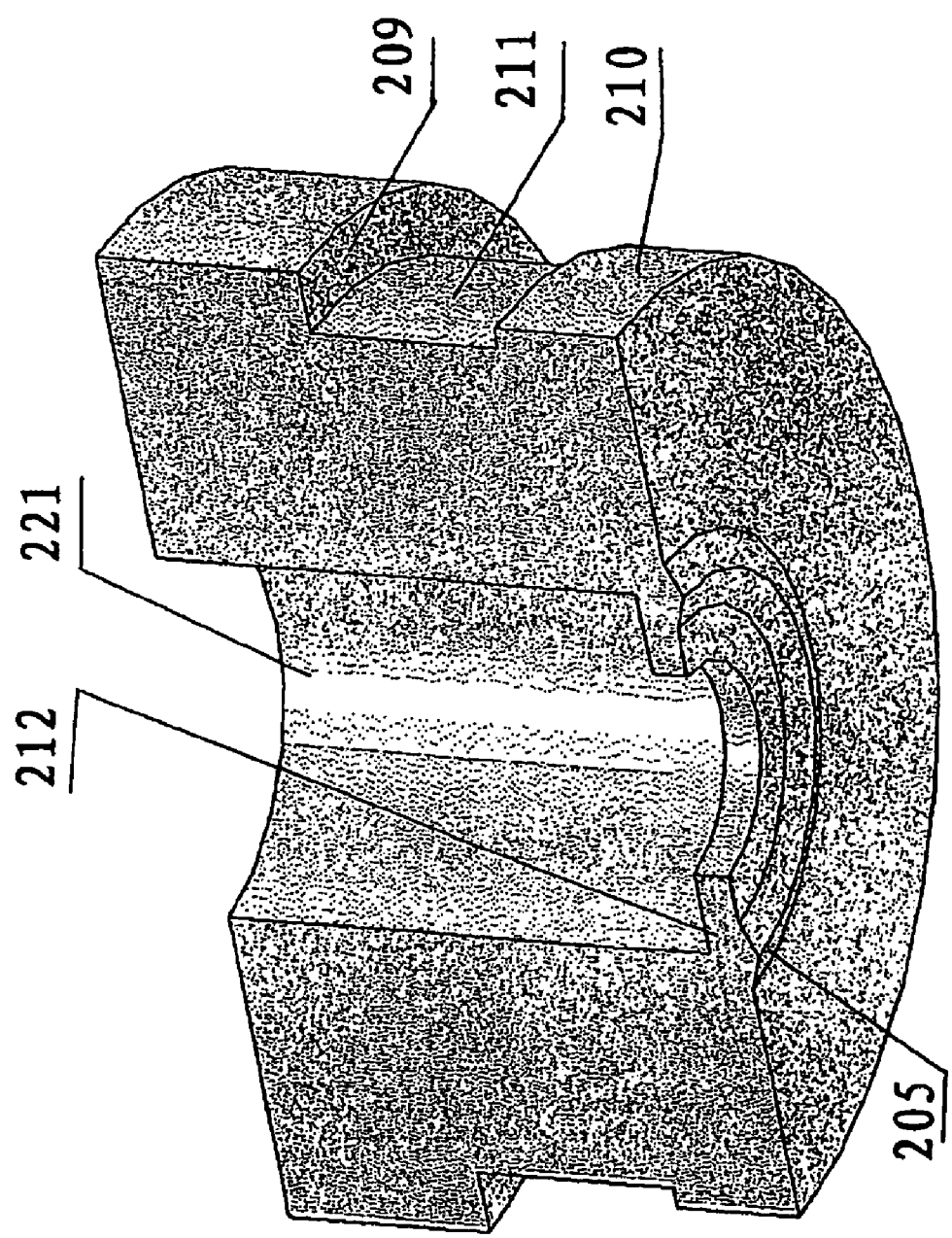
FIG. 14 is a sectional perspective view of a light hood of a probe assembly according to a second preferable embodiment of the present invention.

FIG. 12-14 show a probe assembly according to the second embodiment of the present invention, comprising: a central channel 221 for inserting the pickup 1 therein. The principle of the probe assembly of the second embodiment is similar to that of the first embodiment except for that there are provided no said applying-force mechanism and no the guide bushing as individual parts, instead, the light hood 202 is guided by means of the through-hole 250 of the top plate and also the gravity of the light hood allows it to free slide down.

The light hood 202 has a upper outer flange 209 with such a great diameter that it extends beyond the internal surface of the through-hole 250. Normally, the upper flange 209 abuts on the peripheral edge of the through-hole 250 of the top plate 250 under the action of the gravity of the light hood, so the lower end of the light hood lies in a protruding position, but the light hood can be pushed up by a up pushing force exerted by the edge of the mouth fo the test cell on its lower end which can overcome its gravity when the lower end comes into contact with the edge of the test cell.

The light hood has a lower outer flange 210 at its lower portion. A circumferential chamfer 219 is formed at the bottom of the flange 209 to facilitate a smooth sliding of the lower portion of the light hood with respect to the test cells and prevent it from being stuck during said sliding. The internal contour and size of the through-hole 250 and the external contour and size of the flange 210 are matched with each other, resulting in the flange 210 being guided by the through-hole 250. A annular groove with a reduced diameter is formed at the middle portion of the light hood and there is a small clearance between the surface of the annular groove of the middle portion and the inner surface of the through-hole of the top plate to form a loose fit between the light hood and the through-hole of the top plate. The outside surface of the lower outer flange is in contact with the inner wall of the through-hole of the top plate 205 during sliding of the light hood.

A lower inner flange 212 opposite to the lower outer flange 210 may also be fomed at the lower end of the light hood. An outer circumferential chamfer facing outward and an inner chamfer facing inward are formed at the radial outside of the peripheral edge of the flange 212 bottom (a circumferential projection with an outer chamfer facing outward and an inner chamfer facing inward is formed at the peripheral edge of the flange 212 bottom), so that a circumferential tip is formed at the merging place of the outer chamfer and the inner chamfer. The radial inside portion of the lower surface of the flange 212 bottom is flat.

The light hood is slid down or up by the action of its gravity or the action of the up pushing force exerted on the slope of the chamfer when the top of the test cells contacts with the chamfer during the motion of the micro-cellular plate carrying the test cells, and the tip of the chamfer is inserted into the joint between the test cell of the sample being detected and its adjacent cells when the tip 255 of the inner and outer chamfers is aligned with the joint close. The light hood 202 may be made of bronze.

A single photon counting device according to an embodiment of the present invention including the probe assembly described by reference to FIG. 3-14 will be described below in conjunction with FIG. 1 and 2.

As shown in FIG. 1 and 2, the single photon counting device of the present invention is similar to that of the prior art except the above probe assembly. It comprises: a housing; a single photon counter; and a transporter mechanism. A light-sealing between the test cells inside and the surroundings outside the housing can be achieved when more than one test cells enter the housing, to isolate the test cells from the outside of the housing in a light seal manner.

The single photon counter is fixed to the housing and comprises a photoelectric converter mainly consisting of a photomultiplier assembly 24. The above optical pickup 1 is fixedly connected to the end of the photoelectric converter.

The transporter mechanism is movably mounted in the housing.

In operation, one or more (96 piece) test cells 3 or 306 is integrally connected or adjacently arranged on the micro-cellular plate and the micro-cellular plate along with the test cells is delivered by the transporter mechanism 29 into the housing and moved with the top of the test cells closely abutting on the lower surface (see FIG. 1) of the top plate or a clearance left between the tops of the test cells and the lower surface of the top plate to sequentially make the top mouth of each the test cells be positioned below the through-hole 52 or 250 and aligned with the optical pickup 1, thereby the optical signal is pick up one by one by the optical pickup. Each time when the optical pickup 1 is aligned with the test cell of the sample being determined, the light hood lies in the protruding position after sliding down and the inner circumferential chamfer of the lower end of the light hood closely contacts with the outer circumferential chamfer, to isolate the test cell from the surroundings and other test cells, thereby the signal being detected by the optical pickup is prevented from being interfered with by the other signals from test cell and surroundings. At the end of determination for one sample, the determined sample along with its cell placed on the micro-cellular plate is translated in relation to the light hood by the transporter mechanism, causing the outer circumferential chamfer of the determined test cell to slide in relation to the inner circumferential chamfer of the light hood and pushing the light hood up in a short distance against its gravity. Next, when the optical pickup 1 is aligned with the next test cell, the lower end of the light hood is aligned with its top mouth, the light hood again lies in the protruding position through sliding down, and the same effect can be achieved. In this way, the test cells are delivered one by one by the transporter mechanism sequentially to position them one by one below the optical pickup, to determine all the samples.

While the single photon counting device comprising the probe assembly is shown, the skilled in the art can understand the probe assembly described herein can also be applied to other devices which determine the signal in test cells, wherein the micro-cellular plate can be replaced by other kind of micro cellular plate carrying one or more test cells.

Preferably, the inner diameter $d_1$ of the light hood shown in FIG. 3-11 is 8 mm, the outer diameter $d_2$ of the light hood is 10 mm, the outer diameter $d_3$ of the upper outer flange 9 is 16 mm, the diameter at the circumferential tip of the light hood is 0.1-0.3 mm larger than the maximum outer diameter $d_5$ of the mouth of the test cell, and the conic angle $\alpha_1$ of the inner circumferential chamfer face is 127° and the conic angle $\beta_1$ of the outer circumferential chamfer is 127°.

The size of the light hood shown in FIG. 12-14 can be as follows:

the outer diameter $d_7$ of the upper outer flange 209 is 24 mm, the diameter $d_{10}$ of the lower outer flange is 22 mm, the inner diameter $d_{12}$ of the lower inner flange is 5 mm, the diameter $d_{11}$ at the tip is 9 mm, the inner diameter $d_9$ of the light hood is 9 mm the outer diameter $d_8$ of the annular groove of the middle of the light hood is 21 mm, the conic angle $\alpha_2$ of the inner circumferential chamfer face and the conic angle $\beta_2$ of the outer circumferential chamfer are 140°.

All the above data and the preferable embodiments are described and shown as exemplified examples.

Figure 15:
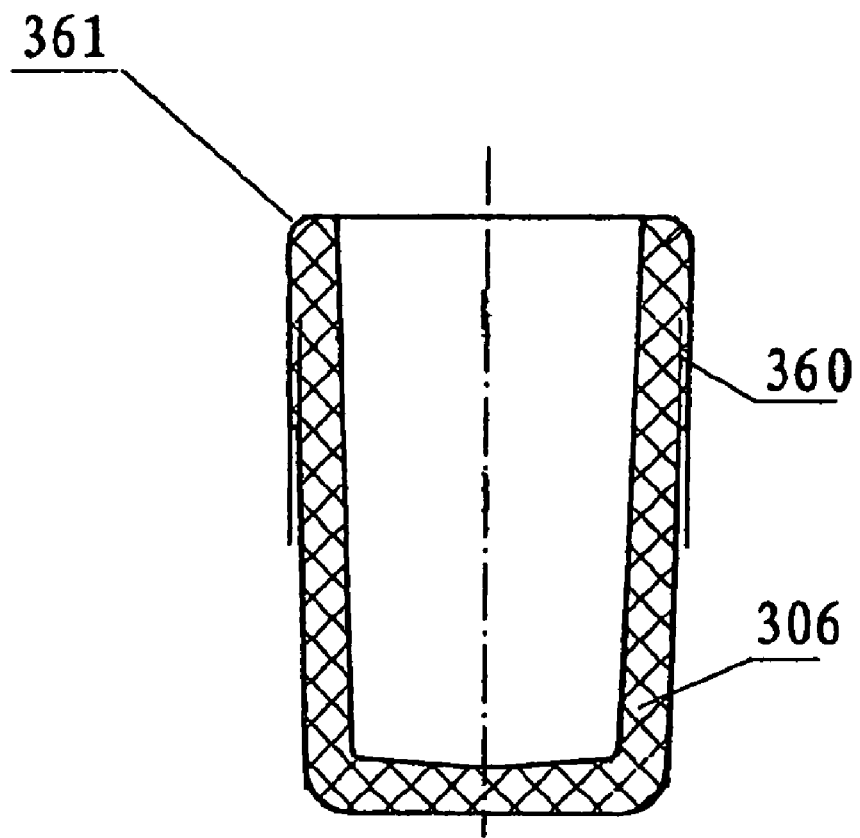
FIG. 15 is a sectional view of a test cell used with the probe assembly according to a second preferable embodiment of the present invention.
Figure 16:
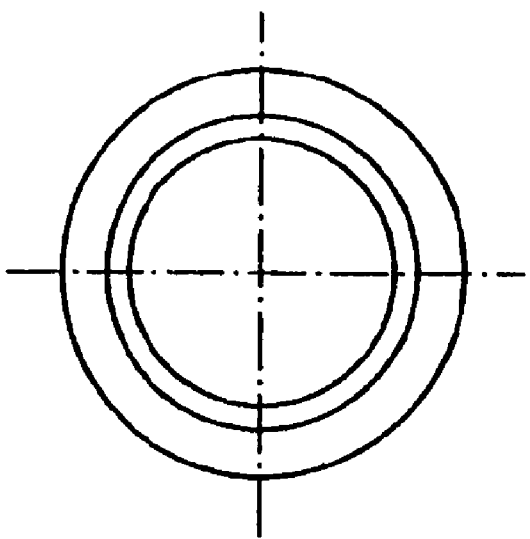
FIG. 16 is a plan view of a test cell used with the probe assembly according to a second preferable embodiment of the present invention.
Figure 17:
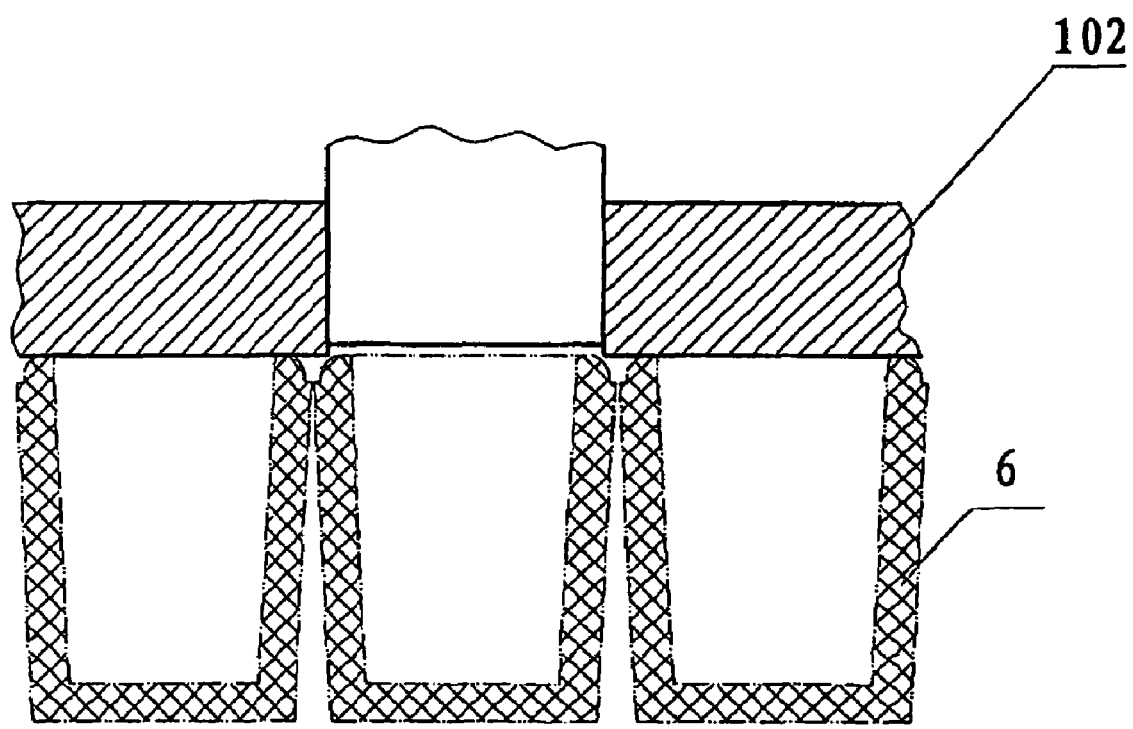
FIG. 17 is a sectional schematic view of a probe assembly of a prior art.

The test cell mentioned above is standard. The test cells shown in FIG. 3 and 12 are integrated and arranged on a micro aperture plate of 96 cells micro-cellular plate by connecting each with other at the outside of each test cell mouth. Alternatively, the present invention may be used with the test cells 306 shown in FIG. 15 and 16 and having a circumferential chamfer 361 with a arc cross-section from which a outer protruding portion 360 extends. The test cells 360 are not integrated with each other like those shown in FIG. 3 and 12. In use, the individual test cell is placed on the micro cellular plate side by side. However, a single test cell 306 can be used for determining one sample once.

The invention claimed is:

1. A probe assembly used in testing instruments for determining optical signal within a test cell, comprising:

a top plate(2; 205) with a through-hole therein(52; 250);

an optical pickup(1) for connecting with a photoelectrical converter and for picking up optical signal within a test cell being detected and sending said optical signal to said photoelectric converter converting said optical signal to electric signal, wherein the position of said optical pickup is fixed in relation to said top plate, the lower end of said optical pickup is inserted into said through-hole (52; 250) of said top plate, during detection more than one test cells adjacently arranged or integrally connected are delivered by a transporter mechanism (29) to the position where one of the test cells is exactly under said through-hole of said top plate with the top mouth of said one of the test cells being exactly aligned with the lower end of said optical pickup, so that the optical pickup picks up the optical signal within said one of the test cells;

characterized in that the probe assembly further comprises:

a cylindrical light hood (2; 202) having a central channel (21; 221), partially inserting into said through-hole (52; 250) of said top plate, and constructed in such a manner that the lower end of said optical pickup is inserted into said channel and surrounded by said light hood and that said light hood can slide down and up along the longitudinal direction of said optical pickup and said through-hole within a small distance between a protruding position and a retracting position, wherein said light hood lies in said retracting position through sliding up, while said light hood lies in said protruding position through sliding downward, during operation, when the one test cell, of which the sample is to be detected, is delivered by said transporter mechanism to the position where it is exactly under said through-hole and aligned with the lower end of said optical pickup, the light hood lies in the protruding position through sliding downward, the size of the lower end of said light hood tightly matches the size of the top mouth of said test cell so that the light interference from the adjacent test cells and surroundings with (to) the determination of the test cell being detected can be avoided by isolating said one test cell from its adjacent cells and surroundings by the lower end of said light hood when said light hood is in said protruding position.

2. The probe assembly of claim 1, characterized in further comprising: a guide bushing (3) having a central sliding passage (36) for said light hood sliding therein and an internal size and contour fitted with the external size and contour of said light hood, inserted into said through-hole of said top plate and fixed on said housing with the wall of said light hood interposed between the outer wall of said optical pickup and the inner wall of said guide bushing, wherein the up and down sliding of said light hood is performed in and guided by said guide bushing.

3. The probe assembly of claim 2, characterized in that said guide bushing (3) is formed with a stop portion and said light hood (2) is formed with a support portion abutting against said stop portion when said light hood lies in said protruding position through sliding downward, so that further sliding downward of said light hood is stopped.

4. The probe assembly of claim 1, characterized in further comprising a force-applying mechanism for enabling said light hood to slide to said protruding position, or for enabling said light hood to slide to said protruding position and back to said retracting position.

5. The probe assembly of claim 4, characterized in that an inner circumferential chamfer and an outer circumferential chamfer merging with the inner chamfer to form a circumferential tip (25) are formed at the lower end of said light hood, a plurality of test cells are provided, said force-applying mechanism comprises at least one force applying spring (4) each in general C shape with its lower end fixed to the housing and its upper end (41) in contact with said light hood (2) in order to apply a predetermined downward pressure to said light hood, so that said light hood normally lies in said protruding position due to the action of the downward pressure, but said light hood slides down or up by the downward pressure of said spring or a up pushing force generated when the top of one of the plurality of the test cells contacts with said chamfers of said light hood, during the movement of the micro-cellular plate carrying said a plurality of the test cells, wherein said circumferential tip (25) formed by the chamfers at the lower end of said light hood is inserted into the joint between the test cell being detected and its adjacent cells, when said circumferential tip is aligned with said joint close.

6. The probe assembly of claim 4, characterized in that said force-applying mechanism is a electric motor which is fixed to said housing and drive said light hood to slide up and down through a transmitting mechanism under controlling of a control circuit as necessary.

7. The probe assembly of claim 5, characterized in that said force-applying springs comprise 4 springs arranged circumferentially at a regular interval around said light hood and fixed to said top plate, and that a fixing flange (31) with through-holes (32) for fixing is formed at the outer circumference of the lower portion of said guide bushing and a fixing ring (12) is formed at each lower end of said force-applying springs, threaded holes are formed at said top plate, so both said guide bushing (3) and said force-applying springs (4) are fixed to said top plate by fastening screws (8) passing through said fixing rings and said fixing though-holes into said threaded holes.

8. The probe assembly of claim 1, characterized in that the lower end of said light hood is inserted into the joint between the test cell being detected and the its adjacent test cells and contacts with the top of the test cell of sample being detected when the light hood lies in said protruding position, thereby a light seal is formed.

9. The probe assembly of claim 2, characterized in that all said light hood (2), said guide bushing (3) and said optical pickup (1) are cylindrical, the radial clearance between the inner wall of said light hood and the outer wall of said optical pickup is 0.3-0.4 mm, and said guide bushing is made of bronze.

10. The probe assembly of claim 1, characterized in that said light hood (202) is formed with an upper outer flange (209) at its upper portion having such a great diameter that said flange radially extends beyond the inner surface of the through-hole (250) of said top plate and said light hood has such a great weight that in a normal condition, said upper flange (209) abuts on the peripheral edge of said through-hole (250), causing said light hood to lie in said protruding position due to the action of its gravity, while said light hood can be slid up by the up pushing force exerted by the mouth of the test cell to its lower end.

11. The probe assembly of claim 10, characterized in that said light hood (202) further have: a middle portion (211) with a reduced diameter forming a annular groove around it, with a clearance between its outer wall and the inner wall of the through-hole of said top plate to form a loose fit between said light hood and said through-hole; a lower outer flange (210) having its outer contour and size fitting with the inner contour and size of said through-hole (250) of said top plate, thus said lower outer flange being guided by said through-hole.

12. The probe assembly of claim 11, characterized in that said light hood further has a lower inner flange (212) a lower inner circumferential chamfer and a lower outer circumferential chamfer merging with each other to form a circumferential tip (255), which are formed at the radial outside of the peripheral edge of the lower inner flange bottom surface, with a portion of the area in the radial inside of the bottom surface of said lower inner flange being flat; with a plurality of test cells placed on the micro-cellular plate, said light hood slides down and up respectively by its gravity and a up pushing force generated when the top of the test cell comes in contact with the chamfers of the lower inner flange of said light hood during the moving of the micro-cellular plate with the test cells, and wherein the circumferential tip formed by both the chamfers inserts into the joint between the test cell being detected and its adjacent cells, when the tip (255) is aligned with the joint close.

13. The probe assembly of claim 4, characterized in that said light hood (202) is formed with an upper outer flange (209) at its upper portion having such a great diameter that said flange radially extends beyond the inner surface of the through-hole (250) of said top plate and said light hood has such a great weight that in a normal condition, said upper flange (209) abuts on the peripheral edge of said through-hole (250), causing said light hood to lie in said protruding position due to the action of its gravity, while said light hood can be slid up by the up pushing force exerted by the mouth of the test cell to its lower end.

* * * * *